United States Patent [19]

Taylor et al.

[11] 4,148,612
[45] Apr. 10, 1979

[54] METHOD AND APPARATUS FOR DETECTING AND MEASURING TRACE IMPURITIES IN FLOWING GASES

[75] Inventors: Gene W. Taylor; Edward J. Dowdy, both of Los Alamos, N. Mex.

[73] Assignee: The United States of America as represented by the United States Department of Energy, Washington, D.C.

[21] Appl. No.: 831,196

[22] Filed: Sep. 7, 1977

Related U.S. Application Data

[63] Continuation of Ser. No. 659,439, Feb. 19, 1976, abandoned.

[51] Int. Cl.² .......................... G01J 3/34; G01N 27/62
[52] U.S. Cl. .............................. 23/232 R; 23/232 E; 356/316; 422/83; 422/98
[58] Field of Search ............. 23/232 R, 232 E, 254 R, 23/254 E; 356/85

[56] References Cited
U.S. PATENT DOCUMENTS

| | | | |
|---|---|---|---|
| 3,025,745 | 3/1962 | Liston | 23/232 R |
| 3,647,387 | 3/1972 | Benson et al. | 23/232 R |

OTHER PUBLICATIONS

Herron et al., J. Chem. Phys. 10, 879 (1959).
West et al., Anal. Chem. 36, 412 (1964).
Heemstra et al., Anal. Chem. 38, 492 (1966).
Bache et al., Anal. Chem. 39, 786 (1967).
Taylor et al., Anal. Chem. 42, 876 (1970).

*Primary Examiner*—Joseph Scovronek
*Attorney, Agent, or Firm*—Dean E. Carlson; Edward C. Walterscheid

[57] ABSTRACT

Trace impurities in flowing gases may be detected and measured by a dynamic atomic molecular emission spectrograph utilizing as its energy source the energy transfer reactions of metastable species, atomic or molecular, with the impurities in the flowing gas. An electronically metastable species which maintains a stable afterglow is formed and mixed with the flowing gas in a region downstream from and separate from the region in which the metastable species is formed. Impurity levels are determined quantitatively by the measurement of line and/or band intensity as a function of concentration employing emission spectroscopic techniques.

8 Claims, 2 Drawing Figures

METHOD AND APPARATUS FOR DETECTING AND MEASURING TRACE IMPURITIES IN FLOWING GASES

This is a continuation of application Ser. No. 659,439 (now abandoned), filed Feb. 19, 1976.

BACKGROUND OF THE INVENTION

The invention described herein relates to method and apparatus for quantitatively monitoring trace impurities in flowing gases through the reaction of the impurities with electronically metastable atoms or molecular species produced in the afterglow of a flowing plasma.

There are many situations in which it is necessary to rapidly and effectively monitor the content of trace impurities in flowing gases. The high temperature gas-cooled reactor (HTGR) is an example of a system in which such monitoring is imperative. The coolant gas flowing through the primary loop of the HTGR is helium. The helium in the primary loop may be contaminated with water vapor from the secondary side of the heat exchangers or from the helium circulator bearings. Reactions of water with the hot graphite fuel blocks or core support structure of the reactor through which the coolant helium flows are highly deleterious. As a consequence, it is imperative that the moisture level in the primary loop be measured accurately on a continuous basis. Preferably, the monitoring method and apparatus should be capable also of quantitatively measuring reaction products of the water and the hot graphite as, e.g., CO, $CO_2$, and $CH_4$.

SUMMARY OF THE INVENTION

In its broad sense, the invention encompasses method and apparatus for detecting and quantitatively measuring trace impurities in a flowing gas by (a) forming a metastable species which maintains a stable afterglow and which reacts with said trace impurities to ultimately produce radiating species particular to the impurities, (b) mixing the metastable species with the gas containing the trace impurities at known flow rates to produce the radiating species, (c) detecting and measuring the intensity of the radiation emitted by the radiating species, and (d) for each radiation corresponding to each impurity, comparing the measured intensity to a predetermined calibration curve at the same flow rates to determine the quantitative amount of each impurity in the flowing gas.

The invention is particularly applicable to the detection and measurement of trace impurities such as $H_2O$, CO, $CO_2$, and $CH_4$ which may exist in the helium used in the primary coolant loop of the HTGR. Thus, e.g., using the apparatus and method of the invention, the presence of trace amounts of $H_2O$ in flowing helium may readily be detected by (a) forming $He(2^3S)$ metastable atoms from pure He, (b) intermixing a flow of these metastable atoms with a flow of the He in which $H_2O$ is to be detected, and (c) measuring the intensity of any resultant band emission in the 306.4 nm $OH(A^2\Sigma^+)\rightarrow OH(X^2\pi)$ system resulting from the $He(2^3S)+H_2O$ reactions.

Particularly advantageous features of the invention are that it permits continuous monitoring of the flowing gas, simultaneous detection of multiple impurities, fast response times to concentration fluctuations of the trace impurities, extremely high sensitivity, and economic monitoring.

DYNAMIC ATOMIC-MOLECULAR EMISSION SPECTROGRAPHY

Figure 1:
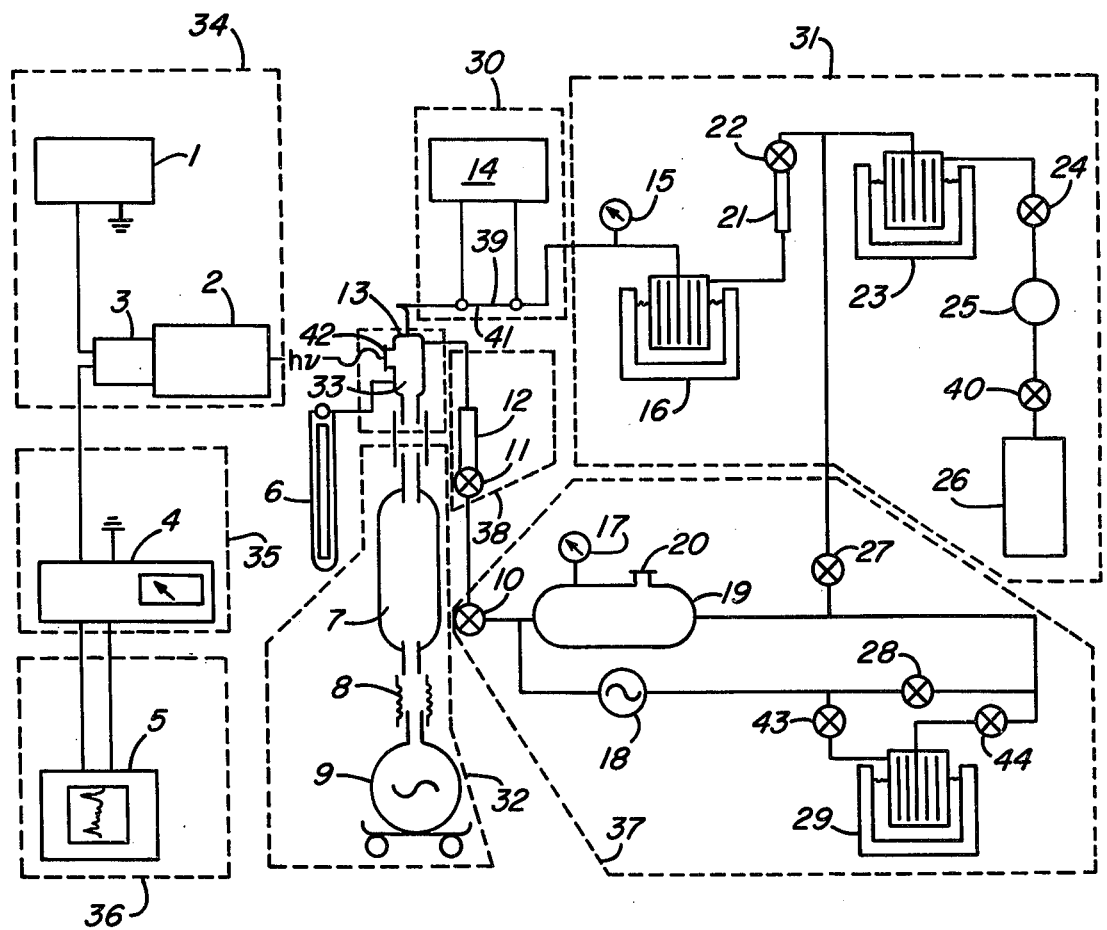
FIG. 1 is a schematic of apparatus useful in practicing the invention.

The apparatus of the invention is essentially a dynamic atomic-molecular emission spectrograph, utilizing as its energy source the energy transfer reactions of metastable species with the impurities in a flowing gas. Quantitative determination of impurity levels is accomplished by the measurement of line and/or band intensity as a function of concentration employing emission spectroscopic techniques. The electronically metastable species (usually rare gas atoms, but occasionally molecular species) are produced in the afterglow of a flowing plasma, which may be initiated by virtually any energy source, e.g., ionizing radiation, electric fields, etc.

A versatile array of noble gas metastable atoms, e.g., $He(2^1S, 2^3S)$, Ne, Ar, Kr, and $Xe(^3P_{0,2})$, may be used as well as molecular metastable sources, such as $N_2(A^3\Sigma_u^+)$ or $CO(a^3\pi)$. In the simplest sense, the metastable atom and/or molecule sources are produced using a fast flowing plasma, with the metastable species formed directly from the plasma as with the rare gas atoms or from the secondary afterglow reactions as in the formation of molecular metastable species. An example of the latter case is the use of $Ar(^3P_{0,2})$ to form $N_2(A^3\Sigma_u^+)$. Molecular metastable species may also be formed from microwave induced plasmas of active gases, such as "active nitrogen," or ion-electron recombinations, such as $CO_2^+ + e^- \rightarrow CO(a^3\pi) + O$. The apparatus and technique are amenable without significant modification to producing detectable emissions from exothermic chemiluminescent sources, such as H-atom, F-atom, O-atom, etc. reactions with impurities. The flowing plasma may be sustained by any ionizing energy source or resonance light absorption.

Using the apparatus and method of the invention, the presence and quantitative amount of $H_2O$ in the primary loop of the HTGR may be rapidly and continuously monitored using the flowing $He(2^3S)$ afterglow technique. The energy transfer from the metastable He atoms to $H_2O$ and the resultant spectroscopic emissions result from the following reactions:

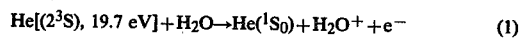 (1)

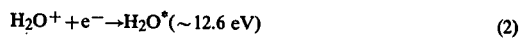 (2)

 (3)

 (4)

Reaction (1) is a Penning ionization in which the excess energy, $E[He(2^3S)] - IP(H_2O) \simeq 7.2$ eV, is partitioned between the relative kinetic energy and intramolecular excitation of $H_2O^+$. Part of the radiation emitted by reaction (4) is at 306.4 nm and is readily measured spectroscopically. By comparing the intensity of this emission against predetermined calibration curves, the quantitative amount of $H_2O$ present in the flowing gas is readily determined.

Simultaneously, the presence and amount of CO, $CO_2$, and $CH_4$ may be determined through the use of the following reactions:

$$He[2^3S], 19.7\ eV] + CO \rightarrow CO^+(B^2\Sigma^+ \rightarrow X^2\Sigma^+),\ 219.0\ nm + He(^1S_O) \quad (5)$$

$$He[2^3S], 19.7\ eV] + CO_2 \rightarrow CO_2^+(\tilde{B}^2\Sigma_u^+ \rightarrow \tilde{X}^2\pi_g),\ 288.3-289.6\ nm + He(^1S_O) \quad (6)$$

$$He[2^3S], 19.7\ eV] + CH_4 \rightarrow CH(A^2\Delta \rightarrow X^2\pi),\ 430.0\ nm + 3H(^2S) + He(^1S_O) \quad (7)$$

Note: The detectable bands described in these reactions are not the only usable emission systems available from these reactions.

DESCRIPTION OF THE PREFERRED EMBODIMENTS

Apparatus for the detection and quantitative measurements of trace impurities in a flowing gas in accordance with the method of the invention is shown schematically in FIG. 1. The major components of the apparatus of FIG. 1 are excitation source 30, rare gas atom source 31, pumping system 32, reaction chamber 13, detection system 34, signal system 35, recording system 36, calibration system 37, and gas input metering unit 38.

Excitation source 30 is the means for producing the metastable rare gas atoms. It may be any means for producing ionization, e.g., ionizing nuclear radiation ($\alpha$, $\beta$, or $\gamma$), x-radiation, cold-cathode discharges, and microwave excitation. Alternatively, excitation source 30 may be an ultraviolet laser, which produces resonance absorption into states above the metastable states and subsequent radiative cascading into the metastable states. In a preferred embodiment, excitation source 30 is a cold-cathode discharge produced in flowing rare gas atoms 39 by means of 0–500 Vdc supply 14.

The source 31 of rare gas atoms 39 may be a direct or purified tank supply of the rare gas or a dilution of the rare gas atoms of choice in a carrier gas stream. As shown in the embodiment of FIG. 1, the rare gas may be obtained from calibration system 37 through valve 27 or from an independent source 26. If obtained from source 26, the gas passes through pressure regulator 25 into a purification system, such as baffled liquid nitrogen trap 23, with flow controlled by needle valve 22 and floating ball flowmeter 21 into liquid nitrogen trap 16. From trap 16, the gas passes through pressure-vacuum gauge 15 and into excitation source 30. The metastable atoms produced therein then flow into reaction chamber 13.

To extend the collision lifetime of the metastable rare gas atoms which would be extremely short at high pressures, gas pressure downstream of the metastable rare gas production region 41 is maintained at a low level ($\leq 10$ torr) by means of high speed pumping system 32. Means for producing and maintaining the requisite low pressure include all the standard vacuum pumping systems such as mechanical forepumps, ion diffusion pumps, or turbo-molecular pumps. In the preferred embodiment, pumping system 32 consists of a 500 liter per minute vacuum pump 9 connected by means of bellows vibration damper 8 to 24-liter ballast volume 7 which is in turn connected to reaction chamber 13.

Reaction of the metastable rare gas atoms with the impurities in the gas stream under analysis occurs in reaction chamber 13 which comprises a simple mixing region 33 which may be constructed of any materials suitable for moderate vacuum service. Chamber 13 contains a window 42 having a high transmission factor for the radiation of interest. Pressure within chamber 13 is measured by means of silicone oil manometer 6, or other suitable device.

Radiation passing through window 42 is detected by detection system 34 which may consist of a scanning monochromator with an associated photosensitive device such as a photomultiplier tube or photosensitive semiconductor detector. Alternatively, a spectrometer with a multiplicity of photosensitive devices may be employed. In the preferred embodiment, detection system 34 consists of a scanning 0.45 m monochromator 2, a photomultiplier tube 3, and a 0–1000 Vdc power supply 1.

Either currents or voltage pulses from the photosensitive devices may be sensed in signal sensing system 35 using either electrometers or photon-counting systems. In the preferred embodiment, an electrometer 4 is used. Recording of the sensed signal may be done with standard chart recorders for the scanning systems or with multichannel pulse height analyzers if multiple detector systems are used. In the preferred embodiment, recording system 35 consists of a strip chart recorder 5. Any of the various detection systems may be made process computer compatible and controlled for various signal enhancement schemes obtainable through software.

It is highly desirable that the device incorporate a calibration system 37 which consists of any method of introducing a known quantity of the impurity gas into reaction chamber 13. This may be accomplished using direct dilution in a carrier gas or any of various standard "leak" techniques well known in the sampling and detecting arts. In the preferred embodiment, calibration system 37 consists of a 24-liter standard volume tank 19 having a pressure-vacuum gauge 17 and a system 20 for introducing a sample or a calibration gas. Baffled liquid nitrogen trap 29 may be introduced into the calibration system or isolated therefrom by means of valves 28, 43, and 44. If trap 29 is used, gas is circulated therethrough by means of circulating bellows pump 18.

The calibration gas or the gas under analysis is introduced into reaction chamber 13 by means of gas input metering unit 38 which consists of needle valve 11 and calibrated flowmeter 12. From the known flow rates of the metastable rare gas atom bearing stream and the gas under analysis and previous calibrations, the quantity of impurities in the gas under analysis may easily be determined.

Figure 2:
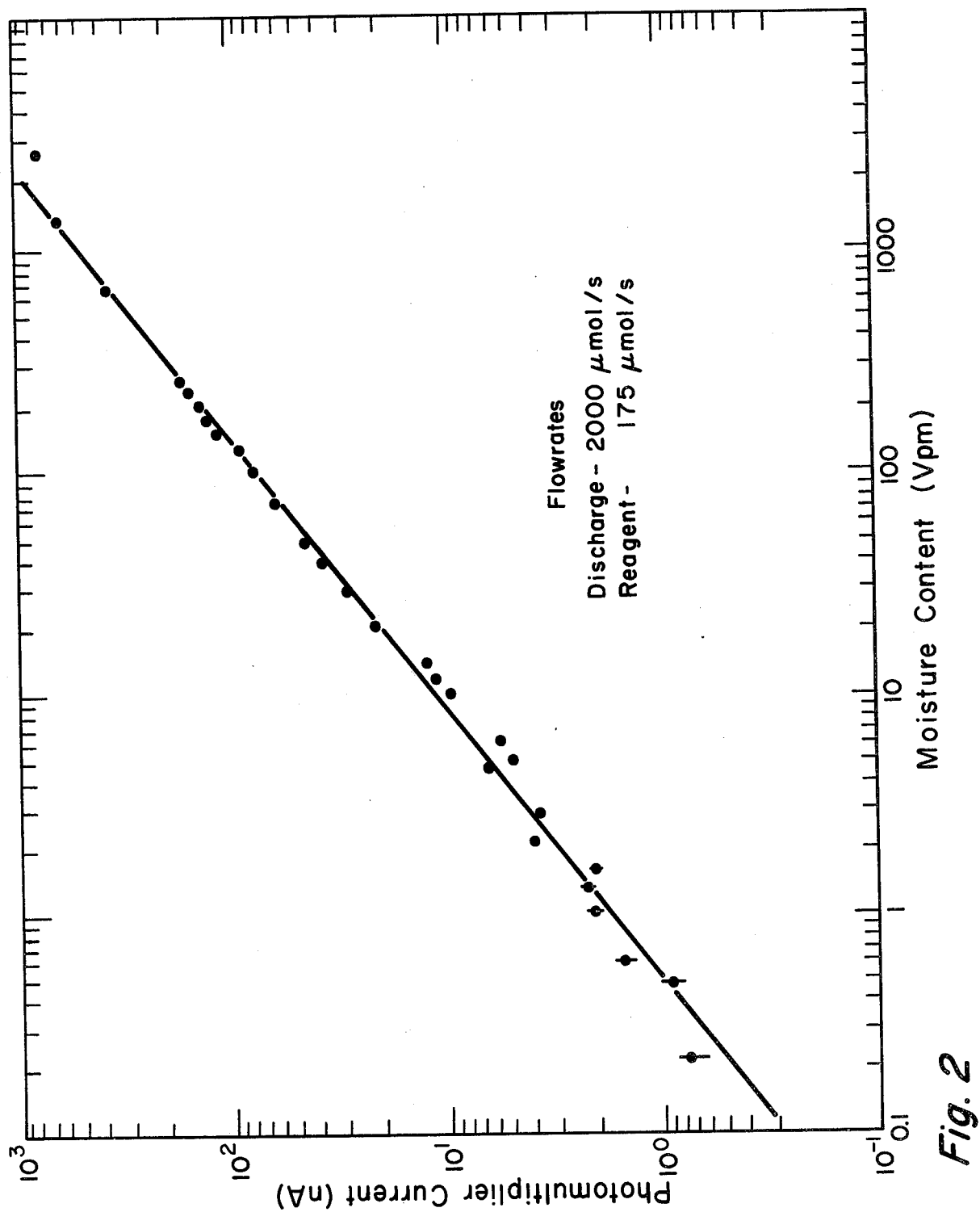
FIG. 2 is a calibration curve for a single set of helium flow conditions over a moisture content range of 0.22 to 1400 ppm.

Using the apparatus of FIG. 1, the calibration data of FIG. 2 were obtained for a single set of flow conditions for helium having a moisture content range of 0.22 to 1400 ppm. Flow rates of 2000 $\mu$mols per second for the metastable atom bearing stream and 175 $\mu$mols per second for the moisture laden stream, which are typical, were used. It will be understood that variations from these flow rates may be desirable to displace the dynamic range from that displayed in FIG. 2. The full curve of FIG. 2 represents a least squares linear fit to an apparent power law behavior. The least squares fit equation is $$M = 0.516\ I^{1.23}$$

where M is the moisture content in ppm, and I is the photomultiplier tube current in nA.

Although the preferred embodiment is directed to the determination of trace impurities in a flowing rare gas, as, e.g., moisture in the flowing helium in the primary coolant loop of the HTGR, neither the apparatus nor the method of the invention is limited to this example. Instead, the method and apparatus are applicable for use with any metastable species which can be made to form a stable afterglow and then react with trace impurities in a flowing gas to ultimately form excited products which radiate sufficiently for the radiation to be detected.

We claim:

1. A method for detecting and quantitatively measuring trace impurities in a flowing gas which comprises (a) forming an electronically metastable species which maintains a stable afterglow and which reacts with said trace impurities to ultimately produce radiating species particular to said impurities, (b) mixing said metastable species with said gas containing said trace impurities at known flow rates to produce said radiating species, said mixing occurring in a region downstream from and separate from the region wherein said metastable species is formed, (c) detecting and measuring the intensity of the radiations emitted by said radiating species, and (d) for each radiation corresponding to each impurity, comparing the measured radiation intensity to a predetermined calibration curve at the same flow rates to determine the quantitative amount of each impurity in said flowing gas.

2. The method of claim 1 wherein said metastable species is formed from rare gas atoms.

3. The method of claim 2 wherein said flowing gas containing said trace impurities is helium, said trace impurities include $H_2O$, $CO$, $CO_2$, and $CH_4$, and said metastable species is $He(2^3S)$.

4. A method for detecting water in flowing helium which comprises (a) forming $He(2^3S)$ metastable atoms from pure He, (b) intermixing a flow of said metastable atoms with a flow of the He in which $H_2O$ is to be detected, said intermixing occurring in a region downstream from and separate from the region in which said metastable atoms are formed, and (c) measuring the intensity of any resultant band emission in the 306.4 nm $OH(A^2\Sigma+) \rightarrow OH(CX^2\pi)$ system resulting from the $He(2^3S)+H_2O$ reactions.

5. Apparatus for detecting trace impurities in a flowing gas which comprises (a) means for forming an electronically metastable species which maintains a stable afterglow and which reacts with said trace impurities to ultimately produce radiating species particular to said impurities, (b) means for mixing said metastable species with said gas containing said trace impurities at known flow rates to produce radiating species, said mixing means being located downstream and separate from the region wherein said metastable species is formed, and (c) means for detecting and measuring the intensity of the radiation emitted by said radiating species.

6. The apparatus of claim 5 wherein said means for forming said metastable species is means for forming said metastable species from rare gas atoms by a cold cathode discharge.

7. The apparatus of claim 6 wherein said means for forming said metastable species is means for forming $He(2^3S)$, and said means for mixing said metastable species with said gas containing said trace impurities at known flow rates to produce said radiating species is means for mixing said $He(2^3S)$ with helium containing such trace impurities as $H_2O$, $CO$, $CO_2$, and $CH_4$.

8. The apparatus of claim 7 having means for flowing helium containing known amounts of said impurities into said means for mixing said metastable species with said gas containing said trace impurities.

* * * * *